United States Patent [19]

Leavitt et al.

[11] Patent Number: 4,616,928
[45] Date of Patent: Oct. 14, 1986

[54] PHOTOELECTRIC SMOKE DETECTOR WITH ADJUSTABLE BACKGROUND SIGNAL

[75] Inventors: George E. Leavitt, Ashland; Felice LoStracco, Worcester, both of Mass.

[73] Assignee: Kidde, Inc., Saddle Brook, N.J.

[21] Appl. No.: 622,769

[22] Filed: Jun. 20, 1984

[51] Int. Cl.$^4$ .............................................. G01N 21/53
[52] U.S. Cl. .................................. 356/338; 250/574; 340/630
[58] Field of Search ....................... 356/338; 250/574; 340/630

[56] References Cited

U.S. PATENT DOCUMENTS

| | | | |
|---|---|---|---|
| 3,992,102 | 11/1976 | Kajii | 250/574 |
| 4,216,377 | 8/1980 | Masegawa et al. | 356/338 |
| 4,488,049 | 12/1984 | Marsocci | 356/338 |

Primary Examiner—R. A. Rosenberger
Assistant Examiner—Crystal Cooper

Attorney, Agent, or Firm—John E. Toupal; Harold G. Jarcho

[57] ABSTRACT

A photoelectric smoke detector including a housing defining a test zone and an opening for admitting smoke thereinto, a light source arranged to direct light to the zone and a light responsive element arranged to receive light scattered by smoke particles in the zone. An optical barrier prevents the direct transmission of light through the zone and between the light source and light responsive element, the barrier defining a light passage for transmitting light directly therebetween. Projecting into the light passage is a mechanical gate that can be adjusted to alter the size of the light passage and thereby vary the level of light transmitted directly therethrough between the light source and the light responsive element. In response to selective adjustment of the mechanical gate, the light responsive element can provide a background signal that obviates normal electronic noise.

16 Claims, 2 Drawing Figures

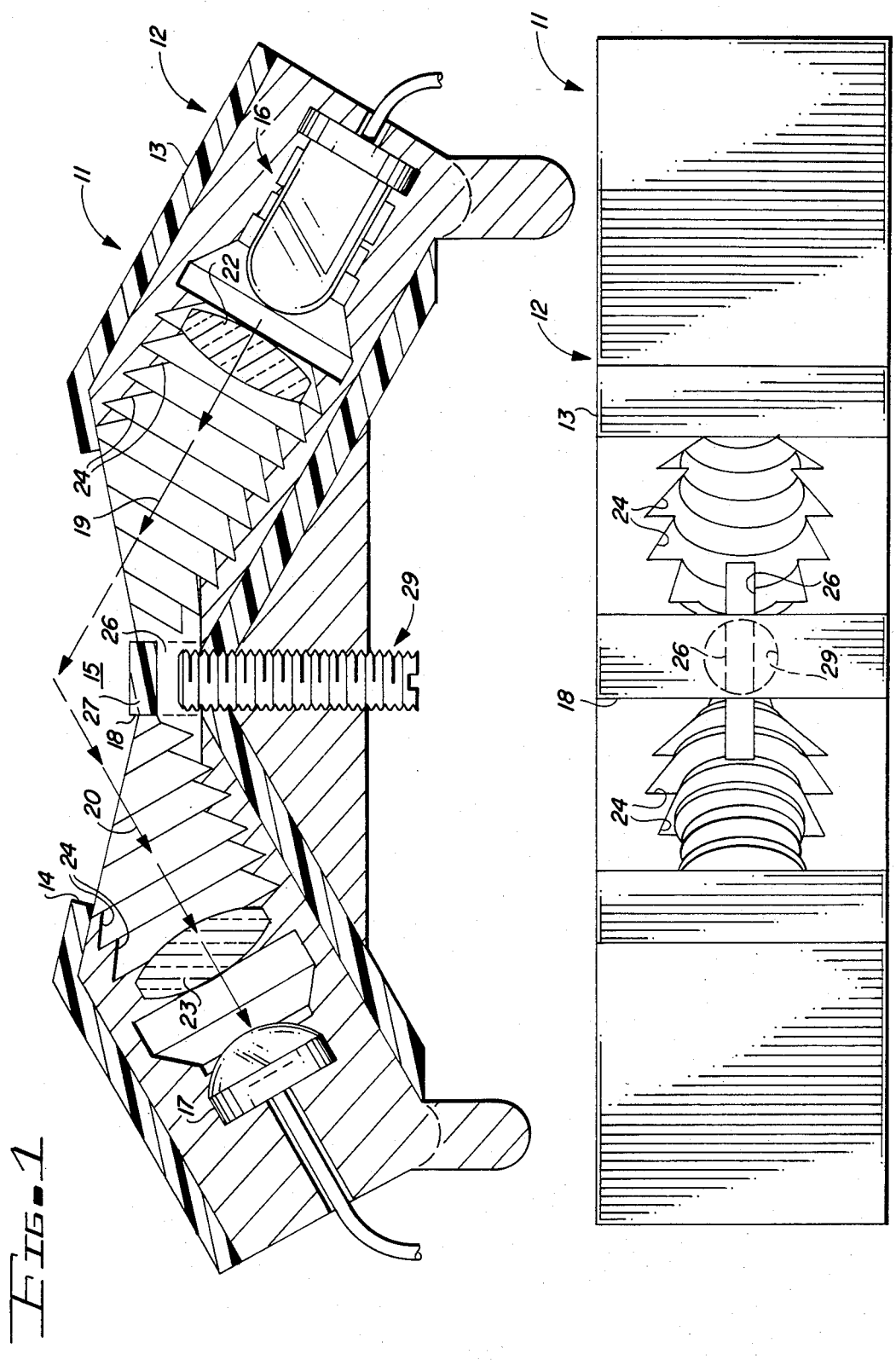

PHOTOELECTRIC SMOKE DETECTOR WITH ADJUSTABLE BACKGROUND SIGNAL

BACKGROUND OF THE INVENTION

This invention relates generally to photoelectric smoke detectors, and more particularly, to a scatter type photoelectric smoke detector that provides an adjustable background signal.

Photoelectric smoke detectors are extensively used to provide an alarm in response to the detection of smoke particles in a protected zone. Basically, a photoelectric smoke detector includes a light source, a light responsive device for receiving light therefrom and an electrical system for producing a signal in response to a predetermined change in the light level received by the light responsive device. Two fundamental types of photoelectric smoke detectors are known and used. In the obscuration type detector, the light source and light responsive device are optically aligned across a test zone. The presence of smoke in the test zone reduces the level of light received by the light responsive device and results in the generation of an alarm signal. Conversely, the light scatter type detector employs a light responsive device that is optically shielded from a light source so as not to receive light directly therefrom. Smoke present in a test zone scatters light from the source to the light responsive device which responds to the increased level by generating an alarm signal.

Typical scatter type detectors enhance their signal to noise ratio by minimizing light leakage between a light source and a light responsive element. Maintenance of an adequate signal to noise ratio, however, has posed a problem for a number of reasons. During normal operation in the absence of smoke, substantially no light is received by the light responsive element and the detector produces no detection signal. Consequently, the amplifiers in detector circuits associated with the smoke detector tend to drift and when exposed to a smoke condition generate variable results. In addition, the signal produced by scatter detectors in response to smoke is generally very small. Externally produced noise signals imposed on a detector, therefore, can reduce significantly the systems signal to noise ratio. Accordingly, a typical scatter system will often either produce a false alarm in response to an insufficient quantity of smoke or experience saturation of its detector amplifiers making them insensitive to an actual smoke signal.

A partial solution to the above problem is disclosed in U.S. Pat. No. 4,306,230. Disclosed in that patent is a scatter type smoke detector having an orifice that transmits a limited level of light directly between a source and a light responsive element. The directly transmitted light establishes a background signal that is used to monitor the functional integrity of the detection system. A disadvantage of the disclosed detector is that the level of background light directly transmitted to the light responsive element cannot be adjusted to provide a desired signal to noise ratio. A system permitting adjustment of a background light level in a photoelectric smoke detector is disclosed in U.S. Pat. No. 3,992,102. In that device an adjustable screw disposed in the smoke detection chamber can be adjusted to vary the level of background light reflected upon a light receiving element. However, adjustment of the screw within the smoke detection chamber also varies the level of smoke reflected light received by the light responsive element thereby affecting the detectors sensitivity. In addition, certain conditions such as accumulated condensation on reflection surfaces can significantly increase the level of reflected background light received by the light responsive device and thereby cause false alarms.

SUMMARY OF THE INVENTION

The invention is a photoelectric smoke detector including a housing defining a test zone and an opening for admitting smoke thereinto, a light source arranged to direct light to the zone and a light responsive element arranged to receive light scattered by smoke particles in the zone. An optical barrier prevents the direct transmission of light through the zone and between the light source and light responsive element, the barrier defining a light passage for transmitting light directly therebetween. Projecting into the light passage is a mechanical gate that can be adjusted to alter the size of the light passage and thereby vary the level of light transmitted directly therethrough between the light source and the light responsive element. In response to selective adjustment of the mechanical gate, the light responsive element can provide a background signal that obviates normal electronic noise.

According to one feature of the invention, the light passage is disposed out of any direct light path between the detection zone and the light responsive element so as to transmit therebetween substantially no light scattered by smoke particles in the zone. Because of this feature, the sensitivity of the detector is not significantly affected by adjustment of the mechanical gate.

According to other features of the invention, the housing defines a light source passageway extending between the light source and the detection zone, a light receiving passageway extending between the light responsive element and the detection zone and oriented at an angle with respect to the light source passageway, and a wall portion separating the light source and receiving passageways; and the light passage is a slot extending through the wall portion between the source passageway and the receiving passageway. These structural features provide the desired functional objectives in a compact, easily manufactured structural arrangement.

According to yet another feature of the invention, the housing includes a separation wall arranged to isolate the detection zone from the light passage. The separation wall limits the entry of smoke particles into the light passage and thereby reduces changes in sensitivity resulting from adjustment of the mechanical gate.

DESCRIPTION OF THE DRAWINGS

These and other objects and features of the invention will become more apparent upon a perusal of the following description taken in conjunction with the accompanying drawings wherein:

FIG. 1 is a schematic cross-sectional view of a photoelectric smoke detector according to the invention; and FIG. 2 is a top view of the detector shown in FIG. 1.

DESCRIPTION OF THE PREFERRED EMBODIMENT

Illustrated in FIGS. 1 and 2 is a photoelectric smoke detector 11 constructed in accordance with the present invention. A housing 12 includes an optical block 13 shaped to support the functional components of the detector 11. A smoke access opening 14 in the optical block 13 provides communication between the surrounding environment and a test zone 15 within the housing 12. Not shown is a conventional cover that is supported by the housing 12 and optically shields the test zone 15 from the surrounding environment. Supported at one end of the block 13 is a light source 16 which can consist, for example, of a light emitting diode. A light responsive element 17 such as, for example, a photo diode is mounted in an opposite end of the block 13. Defined by the block 13 is a barrier wall portion 18 that optically shields the light responsive device 17 from the light source 16 so as to prevent the direct transmission of light therebetween. Also defined by the housing 12 are a light source passageway 19 extending between the light source 16 and the test zone 15 and a light receiving passageway 20 extending between the photo diode 17 and the test zone 15. The light source passageway 19 is oriented at an angle to the light receiving passageway 20. Light emitted from the source 16 is directed by an optical lens 22 to the test zone 15. Another optical lens 23 directs light received from the test zone 15 to the light responsive device 17. Serrated surfaces 24 in the optical block 13 along the passageways 19, 20 provide absorption surfaces that tend to columnize transmitted light and reduce the influx of scattered light from other than the test zone 15.

Formed in the block and extending through the barrier wall portion 18 is a slot 26 that extends between the light source passageway 19 and the light receiving passageway 20. The slot 26 defines a light passage 27 extending rectilinearly between the light source lens 22 and the light receiving lens 23 so as to permit direct light transmission therebetween. However, a separation portion of the barrier 18 isolates the light passage slot from the test zone 15. Supported by the optical block 13 and projecting into the light passage slot 26 is a manually adjustable gate screw 29. Axial movement of the screw varies the size of the light passage slot and consequently in the level of light transmitted directly between the source 16 and the light receiving element 17.

OPERATION

Smoke present in a protected area will enter the test zone 15 of the photoelectric detector 11 disposed therein. The smoke particles in the test zone 15 act in the well known manner to scatter light emitted by the light source 16 to the light responsive device 17. The increased light results in an increased electrical output from the photo diode 17. In response to a predetermined increase in the output of the photo diode 17, a conventional detection circuit (not shown) activates an alarm to indicate the presence of combustion products in the protected area.

Even in the absence of smoke particles in the test zone 15, the light receiving element 17 receives light directly from the source 16 via the light passage 27. Consequently, the receiving element produces under normal conditions a background signal having a value substantially less than required to activate an alarm. The continuous background signal produced by the receiving element 17 reduces the degree of drift experienced by amplifiers in the detection circuit (not shown). Accordingly, response predictability of the detection circuit in response to smoke is significantly enhanced. By selectively varying the projection of the gate screw 29 into the slot 26, the size of the passage 27 is changed to provide a desired level of direct light transmission between the source 16 and the receiving element 17. Such an adjustment in turn establishes a background signal level that obviates normal electronic noise to provide stable response characteristics.

Obviously, many modifications and variations of the present invention are possible in light of the above teachings. It is to be understood, therefore, that the invention can be practiced otherwise than as specifically described.

What is claimed is:

1. A photoelectric smoke detector comprising:
   a housing means defining a test zone and an opening for admitting smoke thereinto;
   light source means arranged to direct light into said zone;
   light responsive means arranged to receive light scattered by smoke particles in said zone;
   optical barrier means arranged to prevent the direct transmission of light through said zone and between said light source means and said light responsive means, said barrier means defining a light passage for transmitting light directly between said light source means and said light responsive means; and
   mechanical gate means projecting an adjustable distance into said passage so as to permit variation in the size thereof and consequently in the level of light transmitted directly therethrough between said light source means and said light responsive means.

2. A smoke detector according to claim 1 wherein said mechanical means comprises a screw adjustably retained by threads in said optical barrier means.

3. A smoke detector according to claim 2 wherein said optical barrier comprises a wall disposed between said light source means and said light responsive means, and said passage comprises a slot in said wall and extending between said light source means and said light responsive means.

4. A smoke detector according to claim 3 wherein said housing means further defines a light source passageway extending between said light source means and said zone, a light receiving passageway extending between said light responsive means and said zone and oriented at an angle with respect to said source passageway; and said light passage extends between said source passageway and said receiving passageway.

5. A smoke detector according to claim 1 wherein said light passage is disposed out of any direct light path between said zone and said light responsive means so as to transmit therebetween substantially no light scattered by smoke particles in said zone.

6. A smoke detector according to claim 5 wherein said mechanical means comprises a screw adjustably retained by threads in said optical barrier means.

7. A smoke detector according to claim 6 wherein said optical barrier comprises a wall disposed between said light source means and said light responsive means, and said passage comprises a slot in said wall and extending between said light source means and said light responsive means.

8. A smoke detector according to claim 7 wherein said housing means further defines a light source passageway extending between said light source means and said zone, a light receiving passageway extending between said light responsive means and said zone and oriented at an angle with respect to said source passageway; and said light passage extends between said source passageway and said receiving passageway.

9. A smoke detector according to claim 1 including separation means disposed to isolate said zone from said light passage.

10. A smoke detector according to claim 9 wherein said mechanical means comprises a screw adjustably retained by threads in said optical barrier means.

11. A smoke detector according to claim 10 wherein said optical barrier comprises a wall disposed between said light source means and said light responsive means, and said passage comprises a slot in said wall and extending between said light source means and said light responsive means.

12. A smoke detector according to claim 11 wherein said housing means further defines a light source passageway extending between said light source means and said zone, a light receiving passageway extending between said light responsive means and said zone and oriented at an angle with respect to said source passageway; and said light passage extends between said source passageway and said receiving passageway.

13. A smoke detector according to claim 9 wherein said light passage is disposed out of any direct light path between said zone and said light responsive means so as to transmit therebetween substantially no light scattered by smoke particles in said zone.

14. A smoke detector according to claim 13 wherein said mechanical means comprises a screw adjustably retained by threads in said optical barrier means.

15. A smoke detector according to claim 14 wherein said optical barrier comprises a wall disposed between said light source means and said light responsive means, and said passage comprises a slot in said wall and extending between said light source means and said light responsive means.

16. A smoke detector according to claim 15 wherein said housing means further defines a light source passageway extending between said light source means and said zone, a light receiving passageway extending between said light responsive means and said zone and oriented at an angle with respect to said source passageway; and said light passage extends between said source passageway and said receiving passageway.

* * * * *